US 8,992,691 B2

(12) United States Patent
Henry et al.

(10) Patent No.: US 8,992,691 B2
(45) Date of Patent: Mar. 31, 2015

(54) PARTIAL SOLUTION REPLACEMENT IN RECYCLABLE PERSULFURIC ACID CLEANING SYSTEMS

(75) Inventors: Richard O. Henry, Newburgh, NY (US); David F. Hilscher, Lagrange, NY (US); Sandi E. Merritt, Cold Spring, NY (US); Charles J. Taft, Wappingers Falls, NY (US); Robert W. Zigner, Jr., Hyde Park, NY (US)

(73) Assignee: International Business Machines Corporation, Armonk, NY (US)

( * ) Notice: Subject to any disclaimer, the term of this patent is extended or adjusted under 35 U.S.C. 154(b) by 535 days.

(21) Appl. No.: 13/080,097

(22) Filed: Apr. 5, 2011

(65) Prior Publication Data

US 2012/0255577 A1    Oct. 11, 2012

(51) Int. Cl.
*H01L 21/67* (2006.01)
*H01L 21/02* (2006.01)

(52) U.S. Cl.
CPC .... *H01L 21/67057* (2013.01); *H01L 21/02052* (2013.01); *H01L 21/67017* (2013.01)
USPC .......................................... 134/10; 134/56 R

(58) Field of Classification Search
CPC ........ C25D 21/00; C25D 21/12; C25D 21/14; C25D 21/16; C25D 21/18; C25D 21/20; C25D 21/22; C02F 2103/346
USPC ................................................. 134/10, 56 R
See application file for complete search history.

(56) References Cited

U.S. PATENT DOCUMENTS

| | | | |
|---|---|---|---|
| 4,115,225 A | 9/1978 | Parsi | |
| 4,479,852 A * | 10/1984 | Bindra et al. | 205/81 |
| 4,739,143 A | 4/1988 | Sakai et al. | |
| 5,192,403 A | 3/1993 | Chang et al. | |
| 5,336,380 A | 8/1994 | Phan et al. | |
| 5,843,291 A | 12/1998 | Eki et al. | |

(Continued)

FOREIGN PATENT DOCUMENTS

| | | |
|---|---|---|
| EP | 0470070 | 2/1992 |
| EP | 1468965 B1 | 10/2004 |

(Continued)

OTHER PUBLICATIONS

Provisional Application FIS820100077.

*Primary Examiner* — Michael Kornakov
*Assistant Examiner* — Katelyn Whatley
(74) *Attorney, Agent, or Firm* — Cantor Colburn LLP; William Steinberg

(57) ABSTRACT

A method of implementing cleaning solution replacement in a recyclable fluid cleaning system for semiconductor wafers includes activating electrode current for an electrolysis reactor included in the cleaning system. At least one of electrode voltage and operating time for the electrolysis reactor is monitored, until a trigger point has been reached. The trigger point includes one of the electrode voltage reaching a predetermined threshold voltage value, a process time counter reaching a predetermined counter value, and a time value that the electrode voltage has been at the threshold voltage value reaching predetermined value. The process time counter is incremented based on one or more of actual wafer processing time, wafer type, number of wafers processed, and thickness of material to be stripped. Upon reaching the trigger point, the electrode current is deactivated, and at least a portion of cleaning system fluid is drained and replaced with fresh cleaning fluid.

8 Claims, 4 Drawing Sheets

(56) References Cited

U.S. PATENT DOCUMENTS

| | | | |
|---|---|---|---|
| 5,846,390 A | 12/1998 | Eki et al. | |
| 5,846,398 A | 12/1998 | Carpio | |
| 5,853,562 A | 12/1998 | Eki et al. | |
| RE36,402 E | 11/1999 | Williams et al. | |
| 6,200,440 B1 | 3/2001 | Moran et al. | |
| 6,277,265 B1 | 8/2001 | Hanak | |
| 6,511,591 B1 | 1/2003 | Virtanen et al. | |
| 6,808,611 B2 * | 10/2004 | Sun et al. | 205/81 |
| 6,972,083 B2 | 12/2005 | Desai et al. | |
| 7,074,316 B2 | 7/2006 | Haibara et al. | |
| 7,229,543 B2 | 6/2007 | Graham et al. | |
| 7,384,535 B2 | 6/2008 | Sonnenberg et al. | |
| 7,427,346 B2 | 9/2008 | Tom et al. | |
| 7,488,405 B2 | 2/2009 | Shigematsu et al. | |
| 2007/0261963 A1 * | 11/2007 | Han et al. | 205/81 |
| 2008/0251108 A1 * | 10/2008 | Nagai et al. | 134/56 R |
| 2009/0078582 A1 | 3/2009 | Kobayashi et al. | |
| 2009/0192564 A1 | 7/2009 | Armstrong et al. | |

FOREIGN PATENT DOCUMENTS

| | | |
|---|---|---|
| EP | 1801265 A1 | 6/2007 |
| JP | 3020746 | 1/1991 |
| JP | 2006278840 | 10/2006 |

* cited by examiner

PARTIAL SOLUTION REPLACEMENT IN RECYCLABLE PERSULFURIC ACID CLEANING SYSTEMS

BACKGROUND

The present invention relates generally to semiconductor device manufacturing and, more particularly, to a method and system for partial solution replacement in recyclable persulfuric acid cleaning systems.

Wafer cleaning in integrated circuit device manufacturing involves the removal of photoresist residue, fine particles, metal, oxide films, and other such materials formed on the surface of a substrate. Typically, a quantity of concentrated sulfuric acid ($H_2SO_4$) is mixed with a quantity of hydrogen peroxide ($H_2O_2$) to produce a solution also known as SPM (Sulfuric Peroxide Mixture), or "piranha" clean ($H_2SO_5$). In addition, peroxydisulfuric acid (also known as Marshall's acid) may also be produced by electrolyzing an aqueous solution containing sulfate ions in an electrolysis reactor. Peroxydisulfuric acid ($H_2S_2O_8$) is a powerful oxidizing agent that exhibits a high cleaning performance and is an effective solution for cleaning semiconductor wafers.

Where persulfuric acid is produced by the combination of concentrated sulfuric acid and hydrogen peroxide, the solution loses its oxidizing power as it self-decomposes. As a result, a continuous supply of hydrogen peroxide solution is necessary to compensate for this decomposition. Moreover, the high concentration sulfuric acid has to be replaced once the sulfuric acid concentration in the solution decreases below a certain level. Because SPM is diluted by the water content of the hydrogen peroxide solution, it becomes difficult to maintain a constant liquid composition. Thus, the solution has to be fully discarded and replaced, for example, at prescribed time intervals or following processing of a certain number of wafer batches. These conditions make it difficult to maintain consistent cleaning performance, as well as require a large volume of chemicals to be stored.

One way to prevent dilution of SPM is to blow ozone ($O_3$) into concentrated sulfuric acid. While this leads to a longer solution replacement cycle, the technique is generally inferior in cleaning performance with respect to using hydrogen peroxide. Furthermore, regardless of whether concentrated sulfuric acid is mixed with hydrogen peroxide or with ozone, ultimately the concentration of the resulting SPM is limited. Correspondingly, cleaning performance is also limited.

More recently, recyclable sulfuric acid cleaning systems have been introduced that can largely decrease the sulfuric acid consumption through a persulfate ion recycling process which produces persulfate ions electrochemically from an aqueous sulfuric acid solution while the sulfuric acid is recycled. Generally, these recyclable sulfuric acid cleaning systems include a cleaning vessel that cleans wafers using a persulfuric acid solution as cleaning fluid, an electrolytic reactor that regenerates the persulfuric acid solution by performing electrolytic reaction to produce persulfate ions from sulfate ions contained in the solution, and one or more fluid lines that circulate the persulfuric acid solution between the cleaning apparatus and the electrolytic reaction apparatus.

A recyclable sulfuric acid cleaning system may allow for bath life extension by eliminating decomposing hydrogen peroxide from the resist strip bath and providing a continuous replenishment of the active species. At some point, however, the continued use of the recyclable sulfuric acid cleaning system without bath replacement may result in electrode passivation or coating, which reduces the DC current produced in the electrolytic reactor. Moreover, compensation for this effect by increasing the operating current of the device may cause precipitation of sulfur on the electrodes, which in turn can result in either down time for cleaning the electrodes or the use of expensive replacement electrodes.

SUMMARY

In an exemplary embodiment, a method of implementing cleaning solution replacement in a recyclable fluid cleaning system for semiconductor wafers, includes activating electrode current for an electrolysis reactor included in the cleaning system; monitoring at least one of: electrode voltage for the electrolysis reactor and operating time that the electrode current has been activated, until a trigger point has been reached; wherein the trigger point comprises one of: the electrode voltage reaching a predetermined threshold voltage value, a process time counter reaching a predetermined counter value, and a time for which the electrode voltage has been at the predetermined threshold voltage value reaching a predetermined time value; wherein the process time counter is incremented based on one or more of: actual wafer processing time, wafer type, number of wafers processed, and thickness of material to be stripped; and upon reaching the trigger point, deactivating the electrode current, draining at least a portion of cleaning system fluid within the cleaning system, and replacing the drained cleaning system fluid with fresh cleaning fluid.

In another embodiment, a method of implementing partial cleaning solution replacement in a recyclable persulfuric acid cleaning system for semiconductor wafers includes activating electrode current for an electrolysis reactor included in the cleaning system; monitoring voltage of electrodes of the electrolysis reactor until a trigger point has been reached, the trigger point comprising the voltage reaching a predetermined threshold voltage value that is representative of anticipated surface condition of the electrodes; and upon reaching the trigger point, deactivating the electrode current, draining a percentage of cleaning system fluid within the cleaning system, and replacing the drained cleaning system fluid with fresh cleaning fluid.

In another embodiment, a method of implementing partial cleaning solution replacement in a recyclable persulfuric acid cleaning system for semiconductor wafers includes activating electrode current for an electrolysis reactor included in the cleaning system; monitoring an operating time that the electrode current has been activated and activating a process time counter, until a trigger point has been reached, the trigger point comprising the process time counter reaching a predetermined counter value; wherein the process time counter is incremented based on one or more of: actual wafer processing time, wafer type, number of wafers processed, and thickness of material to be stripped; and upon reaching the trigger point, deactivating the electrode current, draining a percentage of cleaning system fluid within the cleaning system, and replacing the drained cleaning system fluid with fresh cleaning fluid.

In still another embodiment, a recyclable fluid cleaning system for semiconductor wafers includes a cleaning vessel configured to clean semiconductor wafers immersed in a bath of persulfuric acid cleaning solution, the cleaning solution circulated through a primary process tool fluid path; a secondary fluid path that diverts a portion of the persulfuric acid cleaning solution for electrolysis treatment thereof; an electrolysis reactor within the secondary fluid path that receives oxidant depleted sulfuric acid, the electrolysis reactor having electrodes that, when activated causes sulfate ions in the solution to be oxidized and form persulfate ions that are recombined with fluid from the primary fluid path and fed back to the cleaning vessel; and one or more controller devices in operative communication with the cleaning vessel and with the electrolysis reactor. The one or more controller devices are configured to activate electrode current for the electrolysis reactor; monitor at least one of: electrode voltage and operating time that the electrode current has been activated, until a trigger point has been reached; wherein the trigger point comprises one of: the electrode voltage reaching a predetermined threshold voltage value, a process time counter reaching a predetermined counter value, and a time for which the electrode voltage has been at the predetermined threshold voltage value reaching a predetermined time value; wherein the process time counter is incremented based on one or more of: actual wafer processing time, wafer type, number of wafers processed, and thickness of material to be stripped; and upon reaching the trigger point, deactivate the electrode current, drain at least a portion of cleaning system fluid within the cleaning system, and replace the drained cleaning system fluid with fresh cleaning fluid.

BRIEF DESCRIPTION OF THE SEVERAL VIEWS OF THE DRAWINGS

Referring to the exemplary drawings wherein like elements are numbered alike in the several Figures.

DETAILED DESCRIPTION

As indicated above, existing recyclable sulfuric acid cleaning systems may allow for persulfuric acid bath life extension by eliminating decomposing hydrogen peroxide from the resist strip bath and providing a continuous replenishment of the active species. To avoid electrode fouling, the bath life of the cleaning solution may be reduced, but at a non-cost competitive value of resist removed per the number wafers processed. The chemical life of such a cleaning fluid may be extended significantly by implementing a process that replaces only the portion of fluid that has collected process by products such as inorganic materials that are not modified into gaseous species and release to the system exhaust. As these species remain within the process fluid and are accumulated over the lifetime of the process fluid, alternative techniques are needed to discharge them.

Accordingly, disclosed herein is a method and system that may enable a reduced environmental impact of the resist strip process. Briefly stated, the embodiments described below automatically monitor the recyclable sulfuric acid cleaning system for a "trigger point" condition such as, for example, the electrode voltage reaching a certain threshold value, the system being operated for a certain amount of time, or a combination of both where a threshold voltage has been established for a certain amount of time. Once the trigger point is reached, a portion of the system fluid (e.g., 10%) is drained at one or more collection points and replaced with fresh sulfuric acid. In this manner, the continued use of the bulk of the system fluid is enabled, thus minimizing the non-productive time of the system, as well as reducing waste fluid volume and extending the lifetime of the chemistry.

Figure 1:
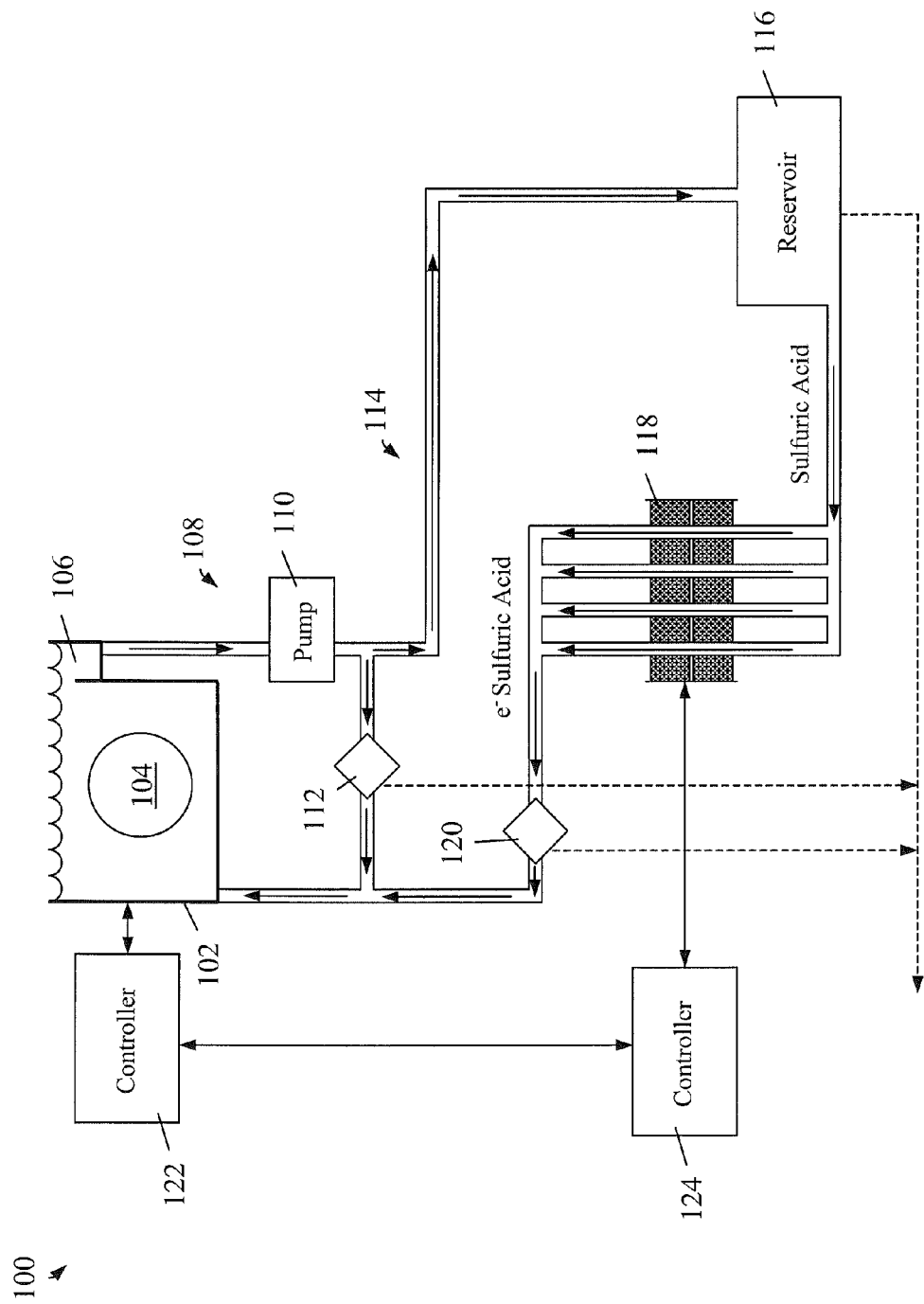
FIG. 1 is a schematic diagram illustrating an exemplary recyclable persulfuric acid cleaning system.

Referring initially to FIG. 1, there is shown an exemplary recyclable persulfuric acid cleaning system 100 suitable for use in accordance with embodiments of the invention. As is shown, the system 100 includes a cleaning vessel 102 configured to clean one or more semiconductor wafers 104 that are immersed in a bath of persulfuric acid cleaning solution 106. The cleaning solution 106 is circulated through a primary process tool fluid path, generally denoted at 108, by one or more fluid pumps 110. The primary fluid path 108 circulates solution at a flow rate on the order about 24 liters per minute (lpm) through a first filter device 112. In addition, the cleaning system includes a secondary fluid path, generally denoted at 114, which diverts a portion of the persulfuric acid cleaning solution 106 for electrolysis treatment thereof.

More specifically, the secondary fluid path 114 includes a fluid reservoir 116 that feeds oxidant depleted sulfuric acid to an electrolysis reactor having electrodes 118 (including cathodes, anodes and bipolar electrodes) as known in the art. When electricity is applied to the electrodes 118 within the electrolysis reactor, depleted sulfuric acid flowing between the electrodes 118 causes sulfate ions in the solution to be oxidized and form persulfate ions, resulting in the regeneration of the persulfuric acid solution. The regenerated persulfuric acid solution (i.e., the electrolyzed sulfuric acid) is passed through a second filter device 120 before being recombined with fluid from the primary fluid path 108 and fed back to the cleaning vessel. In comparison to the fluid flow rate of the primary fluid path 108, the regenerative secondary fluid path 114 may circulate fluid through the electrolysis reactor at the rate of about 1 lpm.

As indicated above, the cleaning system 100 is configured for a partial volume replacement at a desired trigger point (discussed in further detail below). To this end, one or more drain collection points (depicted by the dashed arrows in FIG. 1) are configured to drain a portion of the cleaning fluid from the system, and replaced by fresh sulfuric acid. For example, such drain collection points may include the reservoir 116 in the secondary fluid path 114, the first filter device 112 in the primary fluid path 108, and the second filter device 120 in the secondary fluid path 114. Other drain collection points may also be used, however.

As also indicated above, the amount of fluid drained from the cleaning system 100 upon reaching a given trigger point is just a fraction of the total volume in the described embodiments. This amount may range, for example, from about 5% to about 20% of the total volume, more preferably from about 6% to about 10% of the total volume, and even more preferably about 10%.

The cleaning system 100 may be also fully automated, wherein a first controller 122 that includes one or more processing devices is in operative communication with the cleaning vessel 102 and other components associated with the primary fluid path 108 for wafer processing and fluid control. A second controller 124 that also includes one or more processing devices is in operative communication with the electrodes 118 and other components associated with the electrolysis reactor and secondary fluid path 114. Furthermore, the first and second controllers 122, 124 communicate with one another such that for example, the first controller 122 may inform the second controller 124 that wafer processing is or is not taking place so that the second controller can implement one or methods of monitoring the system 100 for a trigger condition.

Figure 2:
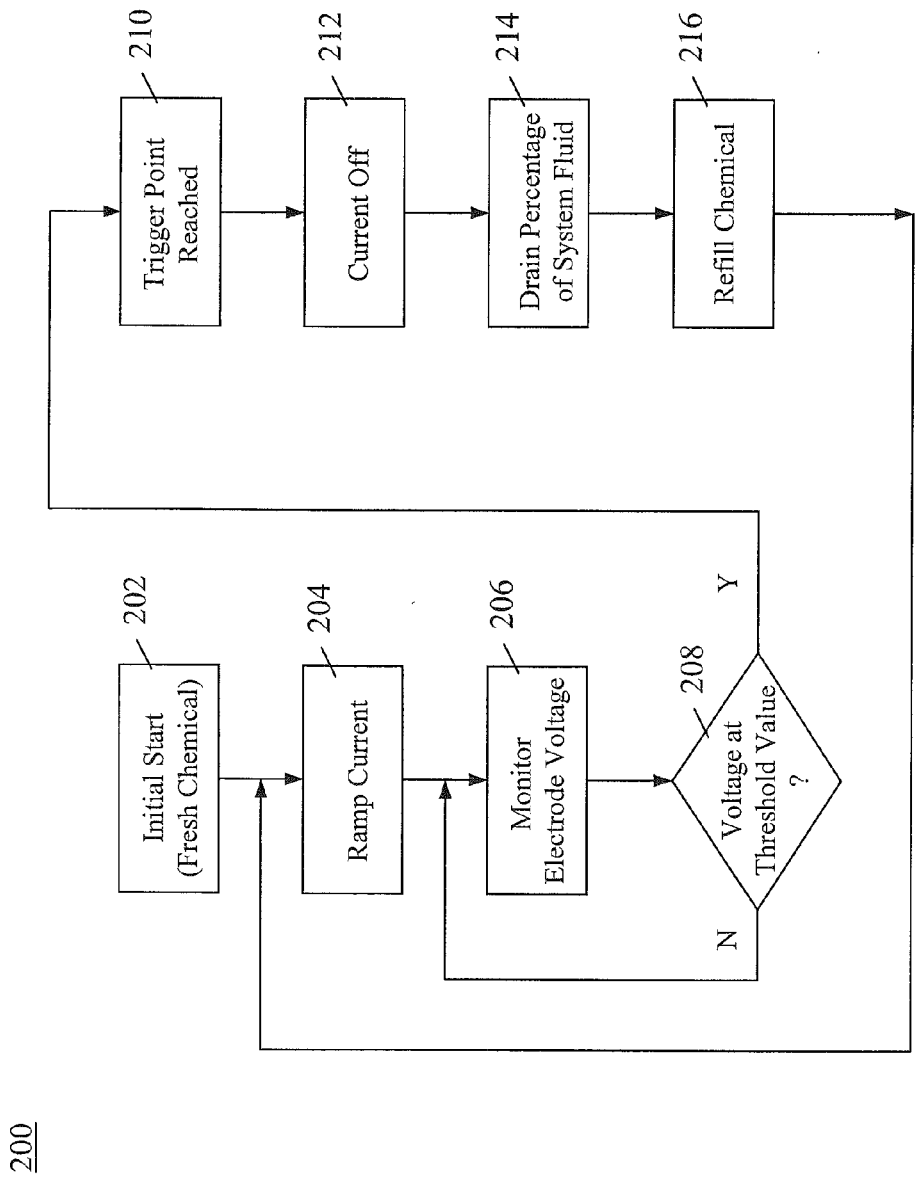
FIG. 2 is a flow diagram illustrating a method of implementing partial solution replacement in recyclable persulfuric acid cleaning systems, in accordance with an exemplary embodiment.

Referring now to FIG. 2, there is shown flow diagram illustrating a method 200 of implementing partial solution replacement in recyclable persulfuric acid cleaning systems, in accordance with an exemplary embodiment. Beginning in block 202, the system (e.g., the recyclable persulfuric acid cleaning system 100 of FIG. 1) is presumed to be in an initial starting state where fresh chemical solution is circulating therethrough. At block 204, electrode current for operating the electrolysis reactor is activated or ramped up. Once the current is activated, the process monitors for a trigger point that signifies when it is time to replace a portion of the system fluid. In the embodiment illustrated, such a trigger point is determined by monitoring the electrode voltage of the electrolysis reactor, as indicated in block 206. By monitoring the electrode voltage over time, the surface condition of the electrodes may be anticipated. As the reactor electrodes become coated with resist residue from the cleaning process, DC voltage is increased to maintain the proper electrolysis reaction. The increased voltage in turn leads to constant current across the electrodes. As such, a predefined electrode voltage may be established that, once reached, establishes a trigger point for partial fluid drainage.

Thus, as reflected in decision block 208, so long as the voltage has not reached the predefined threshold value, the method loops back to block 206 for continued monitoring. On the other hand, if in fact the electrode voltage is at the threshold value, then the method proceeds to block 210 where the trigger point is determined to have been reached. As a result, the electrode current is shut off in block 212. Then, as shown in block 214, a percentage of the system fluid is drained. Again, this percentage may be on the order of about 10% as described above, for example, wherein the partial volume is removed from the aforementioned drain collection points in FIG. 1. Upon draining, the volume is replaced with fresh sulfuric acid, as shown in block 216. The method may end at this point or, as shown in FIG. 2, loop back to block 204 to reactivate the reactor electrodes and once again monitor electrode voltage until it reaches the threshold value.

Figure 3:
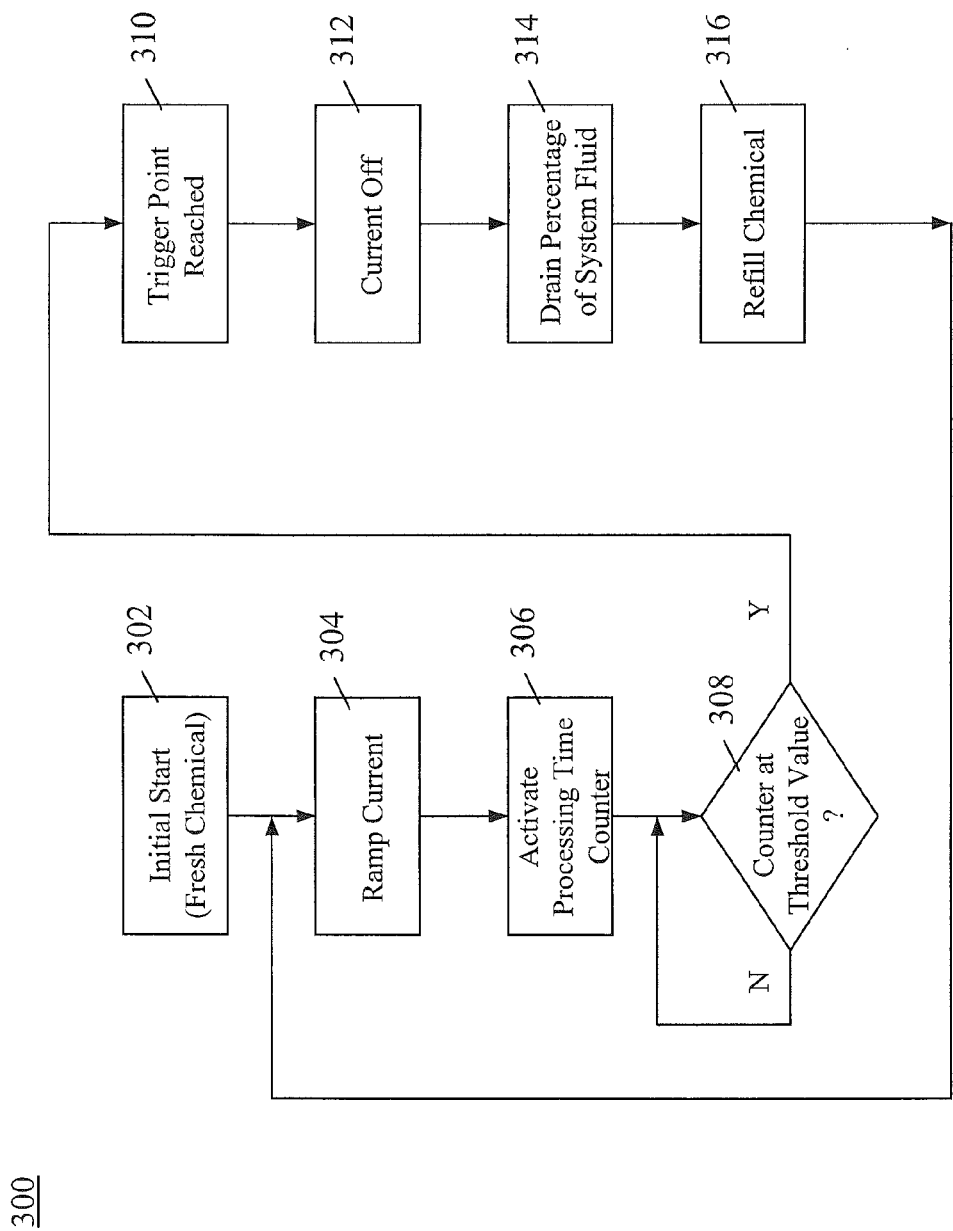
FIG. 3 is a flow diagram illustrating a method of implementing partial solution replacement in recyclable persulfuric acid cleaning systems, in accordance with another exemplary embodiment.

In lieu of monitoring electrode voltage, it is also contemplated that other defined trigger points may be established. For example, FIG. 3 is a flow diagram illustrating a method 300 of implementing partial solution replacement in recyclable persulfuric acid cleaning systems, in accordance with another exemplary embodiment. Blocks 302 and 304 are similar in operation to those of blocks 202 and 204 of FIG. 2, in that the system is initially presumed to have fresh cleaning solution circulating therein as the electrolysis reactor is activated and the electrode current is ramped. In this embodiment, a processing time counter is activated as shown in block 306. The process time counter may be incremented by one or more factors including, but not limited to, actual processing time, wafer type, number of wafers processed, and thickness of material to be stripped.

Thus, as reflected in decision block 308, so long as the process time counter has not reached a predefined threshold value, the method loops back to block 308 for updated monitoring. Once the process time counter has reached the predefined threshold value, the method 300 proceeds to block 310 where the trigger point is determined to have been reached. As a result, the electrode current is shut off in block 312. Then, as shown in block 314, a percentage of the system fluid is drained. Again, this percentage may be on the order of about 10% as described above, for example, wherein the partial volume is removed from the aforementioned drain collection points in FIG. 1. Upon draining, the volume is replaced with fresh sulfuric acid, as shown in block 316. The method may end or, as shown in FIG. 3, loop back to block 304 to reactivate the reactor electrodes and once again monitor processing time until it reaches the threshold value.

Figure 4:
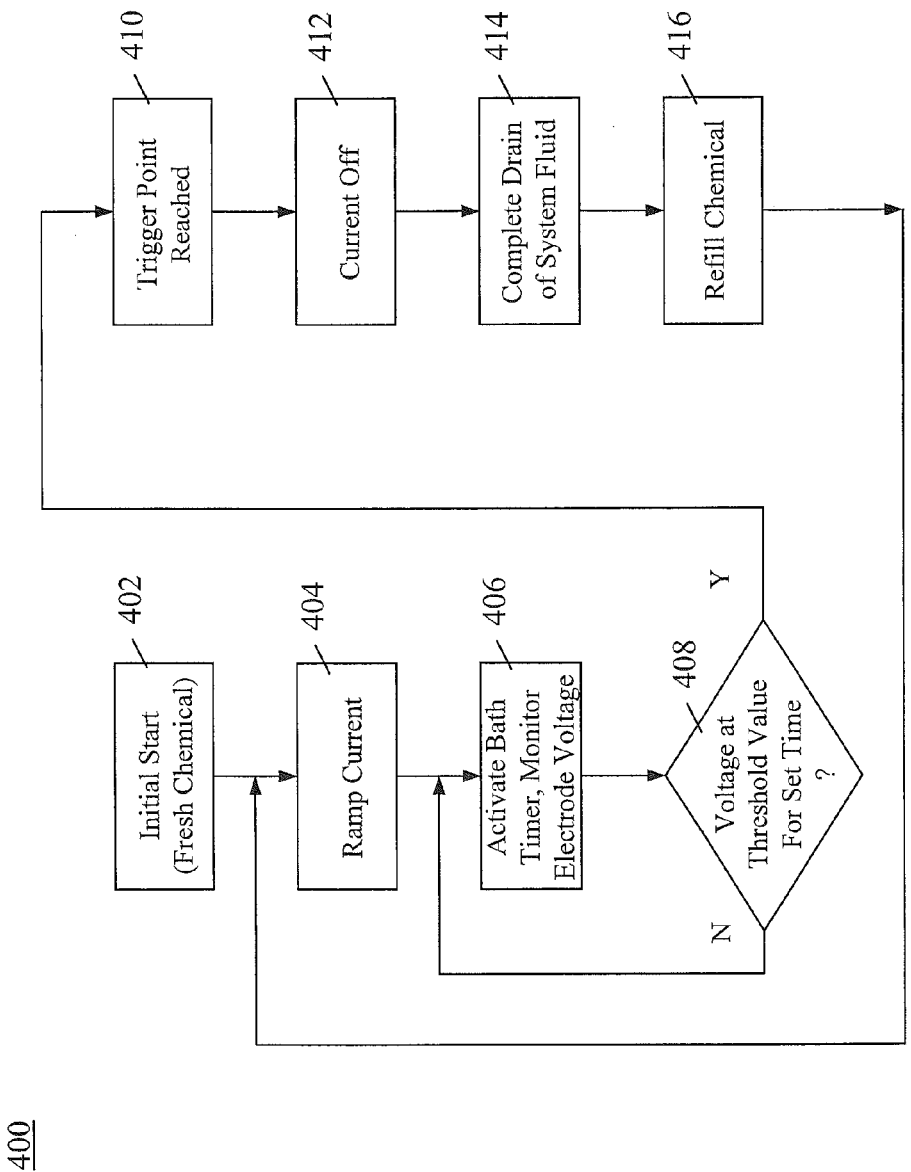
FIG. 4 is a flow diagram illustrating a method of implementing partial solution replacement in recyclable persulfuric acid cleaning systems, in accordance with another exemplary embodiment.

Notwithstanding the above described advantages with respect to partial volume bath replacement, full replacement of the cleaning solution may still be desirable over a longer term. Accordingly, FIG. 4 is a flow diagram illustrating a method 400 of implementing solution replacement in recyclable persulfuric acid cleaning systems, in accordance with still another exemplary embodiment. Blocks 402 and 404 are similar in operation to those of blocks 202 and 204 of FIG. 2 and blocks 302 and 304 of FIG. 3, in that the system is initially presumed to have fresh cleaning solution circulating therein as the electrolysis reactor is activated and the electrode current is ramped. In this embodiment, a bath timer is activated as shown in block 406. As also shown in block 406, the electrode voltage is monitored as well. Thus, the method 400 analyzes the voltage as a function of time and compares a time period for which the electrode voltage has reached a predetermined trigger value (e.g., such as the value of method 200 in FIG. 2).

At decision block 408, the method determines whether the electrode voltage has been at the predetermined threshold value for a predetermined amount of time. If the threshold voltage has not been reached, or if it has been reached but not for the predetermined amount of time, the process loops back to block 406. On the other hand, if in fact the electrode voltage has been at the predetermined threshold value for the predetermined amount of time, the method 400 proceeds to block 410 where the trigger point is determined to have been reached. As a result, the electrode current is shut off in block 412. Then, as shown in block 414, the system fluid is completely drained since the entire bath is considered expired. As is the case for the partial volume replacement embodiments, the entire system fluid may be removed from the aforementioned drain collection points in FIG. 1. Upon draining, the total volume is replaced with fresh sulfuric acid, as shown in block 416. The process may end or, as shown in FIG. 4, loop back to block 404 to reactivate the reactor electrodes and once again monitor processing time until it reaches the threshold value and time. In an exemplary embodiment, such values may initially start out as a relatively long time value or a high count value derived from a number of previously described voltage triggered, partial replacement cycles. In this manner, when such a count decreases to relatively low value trigger over time, this may be an indication of contaminates causing a shortened cycle time so that a complete fluid replacement is warranted.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of implementing cleaning solution replacement in a recyclable fluid cleaning system for semiconductor wafers, the method comprising:

activating electrode current through electrodes of an electrolysis reactor included in the cleaning system;

analyzing an electrode voltage of the electrodes of the electrolysis reactor as a function of time until a trigger point has been reached, wherein the trigger point comprises the electrode voltage of the electrodes of the electrolysis reactor being at a predetermined threshold voltage value corresponding to a surface condition, the surface condition corresponding to resist residue coating the electrodes, of the electrodes for a time period that is at least a predetermined amount of time; and upon reaching the trigger point, deactivating the electrode current, draining at least a portion of cleaning system fluid within the cleaning system, and replacing the drained cleaning system fluid with fresh cleaning fluid.

2. The method of claim 1, wherein the at least a portion of the cleaning system fluid comprises 5% to 20% of a total volume of the cleaning system fluid.

3. The method of claim 1, wherein the at least a portion of the cleaning system fluid comprises 6% to 10% of a total volume of the cleaning system fluid.

4. The method of claim 1, wherein the at least a portion of the cleaning system fluid comprises 10% of a total volume of the cleaning system fluid.

5. The method of claim 1, wherein the at least a portion of the cleaning system fluid comprises the entire volume of the cleaning system fluid.

6. The method of claim 1, wherein the cleaning system fluid circulates through a primary fluid path that comprises a cleaning vessel for semiconductor wafers, and a secondary fluid path that diverts a portion of the cleaning system fluid, and wherein the electrodes are located within the electrolysis reactor in the secondary fluid path.

7. The method of claim 6, wherein a flow rate of the cleaning system fluid in the primary fluid path is faster than a flow rate of the cleaning system fluid in the secondary fluid path.

8. The method of claim 4, further comprising, after replacing the drained cleaning system fluid with fresh cleaning fluid, wherein the at least a portion of the cleaning system fluid comprises from 5% to 20% of a total volume of the cleaning system fluid:

repeating a plurality of partial replacement cycles comprising:

reactivating the electrodes;

resuming analyzing the electrode voltage of the electrodes as a function of time until the trigger point has been reached; and upon reaching the trigger point, deactivating the electrode current, draining at least a portion of cleaning system fluid within the cleaning system, and replacing the drained cleaning system fluid with fresh cleaning fluid, wherein the at least a portion of the cleaning system fluid comprises from 5% to 20% of a total volume of the cleaning system fluid, and wherein for each partial replacement cycle, an amount of processing time is determined; and based on the amount of processing time of a most recent partial replacement cycle of the plurality of partial replacement cycles being equal to a shortened cycle time, replacing the entire volume of the cleaning system fluid.

* * * * *